US010800999B2

(12) United States Patent
Frederiksen et al.

(10) Patent No.: US 10,800,999 B2
(45) Date of Patent: Oct. 13, 2020

(54) METHOD FOR PRODUCTION OF BREWERS WORT

(75) Inventors: Anne Mette Bhatia Frederiksen, Copenhagen (DK); Shiro Fukuyama, Chiba (JP); Keiichi Ayabe, Chiba (JP)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/006,833

(22) PCT Filed: Apr. 11, 2012

(86) PCT No.: PCT/EP2012/056568
§ 371 (c)(1),
(2), (4) Date: Sep. 23, 2013

(87) PCT Pub. No.: WO2012/140075
PCT Pub. Date: Oct. 18, 2012

(65) Prior Publication Data
US 2015/0017282 A1   Jan. 15, 2015

Related U.S. Application Data

(60) Provisional application No. 61/475,762, filed on Apr. 15, 2011.

(30) Foreign Application Priority Data

Apr. 15, 2011   (EP) .................................... 11162594

(51) Int. Cl.
*C12C 7/04* (2006.01)
*C12N 9/34* (2006.01)
*C12N 9/44* (2006.01)
*C12C 12/02* (2006.01)
*C12C 5/00* (2006.01)

(52) U.S. Cl.
CPC ................ *C12C 7/04* (2013.01); *C12C 5/006* (2013.01); *C12C 12/02* (2013.01); *C12N 9/2428* (2013.01); *C12N 9/2457* (2013.01)

(58) Field of Classification Search
CPC ......... C12C 7/04; C12C 5/004; C12C 11/003; C12C 12/02; C12C 5/006; C12C 12/00; C12C 12/04; C12C 7/047

USPC ................ 426/592, 64, 16, 29, 48, 44, 28, 7
See application file for complete search history.

(56) References Cited

U.S. PATENT DOCUMENTS

| 3,379,534 | A | 4/1968 | Hersch Gablinger Basel |
| 4,536,477 | A | 8/1985 | Katkocin et al. |
| 5,665,585 | A | 9/1997 | Torkkeli et al. |
| 6,255,084 | B1 * | 7/2001 | Nielsen ................ C12N 9/2428 435/205 |
| 6,261,629 | B1 | 7/2001 | Mazza et al. |
| 8,343,747 | B2 * | 1/2013 | Burke .................. C12N 9/2414 435/201 |
| 2005/0121305 | A1 | 6/2005 | Saeki |
| 2009/0142447 | A1 * | 6/2009 | Elvig ..................... C12C 5/004 426/13 |
| 2011/0039308 | A1 * | 2/2011 | Slupska ............... C12N 9/2414 435/101 |

FOREIGN PATENT DOCUMENTS

| RU | 2180347 C2 | 3/2002 |
| WO | 2005/121305 A1 | 12/2005 |
| WO | 2007/144393 A1 | 12/2007 |
| WO | 2009/049385 A1 | 4/2009 |
| WO | 2009/075682 A1 | 6/2009 |
| WO | 2011/020852 A1 | 2/2011 |
| WO | 2011/058105 A1 | 5/2011 |
| WO | 2011/127802 A1 | 10/2011 |

OTHER PUBLICATIONS

Matthews et al. Preparation of Low Carbohydrate Beer, vol. 107, No. 3, pp. 185-194 (2001).
Kovaleva et al, 2003, A series of chemistry, biology, and pharmacy, No. 1, pp. 57-60.

* cited by examiner

*Primary Examiner* — Vera Stulii
(74) *Attorney, Agent, or Firm* — Kelly Reynolds

(57) ABSTRACT

The present invention relates to method for production of brewer's wort comprising adding to a mash, a particular glucoamylase. The glucoamylase is obtained from *Penicillium oxalicum*. Further, the invention relates to use of a particular glucoamylase for production of brewer's wort. Furthermore, the invention relates to use of a combination of a glucoamylase and a pullulanase for production of brewer's wort.

17 Claims, No Drawings
Specification includes a Sequence Listing.

SEQUENCE LISTING

<160> NUMBER OF SEQ ID NOS: 4

<210> SEQ ID NO 1
<211> LENGTH: 616
<212> TYPE: PRT
<213> ORGANISM: Penicillium oxalicum

<400> SEQUENCE: 1

```
Met Arg Leu Thr Leu Leu Ser Gly Val Ala Gly Val Leu Cys Ala Gly
1               5                   10                  15

Gln Leu Thr Ala Ala Arg Pro Asp Pro Lys Gly Gly Asn Leu Thr Pro
            20                  25                  30

Phe Ile His Lys Glu Gly Glu Arg Ser Leu Gln Gly Ile Leu Asp Asn
        35                  40                  45

Leu Gly Gly Arg Gly Lys Lys Thr Pro Gly Thr Ala Ala Gly Leu Phe
    50                  55                  60

Ile Ala Ser Pro Asn Thr Glu Asn Pro Asn Tyr Tyr Tyr Thr Trp Thr
65                  70                  75                  80

Arg Asp Ser Ala Leu Thr Ala Lys Cys Leu Ile Asp Leu Phe Glu Asp
                85                  90                  95

Ser Arg Ala Lys Phe Pro Ile Asp Arg Lys Tyr Leu Glu Thr Gly Ile
            100                 105                 110

Arg Asp Tyr Val Ser Ser Gln Ala Ile Leu Gln Ser Val Ser Asn Pro
        115                 120                 125

Ser Gly Thr Leu Lys Asp Gly Ser Gly Leu Gly Glu Pro Lys Phe Glu
    130                 135                 140

Ile Asp Leu Asn Pro Phe Ser Gly Ala Trp Gly Arg Pro Gln Arg Asp
145                 150                 155                 160

Gly Pro Ala Leu Arg Ala Thr Ala Met Ile Thr Tyr Ala Asn Tyr Leu
                165                 170                 175

Ile Ser His Gly Gln Lys Ser Asp Val Ser Gln Val Met Trp Pro Ile
            180                 185                 190

Ile Ala Asn Asp Leu Ala Tyr Val Gly Gln Tyr Trp Asn Asn Thr Gly
        195                 200                 205

Phe Asp Leu Trp Glu Glu Val Asp Gly Ser Ser Phe Phe Thr Ile Ala
    210                 215                 220
```

Val Gln His Arg Ala Leu Val Glu Gly Ser Gln Leu Ala Lys Lys Leu
225                 230                 235                 240

Gly Lys Ser Cys Asp Ala Cys Asp Ser Gln Pro Pro Gln Ile Leu Cys
            245                 250                 255

Phe Leu Gln Ser Phe Trp Asn Gly Lys Tyr Ile Thr Ser Asn Ile Asn
        260                 265                 270

Thr Gln Ala Ser Arg Ser Gly Ile Asp Leu Asp Ser Val Leu Gly Ser
    275                 280                 285

Ile His Thr Phe Asp Pro Glu Ala Ala Cys Asp Ala Thr Phe Gln
290                 295                 300

Pro Cys Ser Ala Arg Ala Leu Ala Asn His Lys Val Tyr Val Asp Ser
305                 310                 315                 320

Phe Arg Ser Ile Tyr Lys Ile Asn Ala Gly Leu Ala Glu Gly Ser Ala
                325                 330                 335

Ala Asn Val Gly Arg Tyr Pro Glu Asp Val Tyr Gln Gly Gly Asn Pro
            340                 345                 350

Trp Tyr Leu Ala Thr Leu Gly Ala Ser Glu Leu Leu Tyr Asp Ala Leu
        355                 360                 365

Tyr Gln Trp Asp Arg Leu Gly Lys Leu Glu Val Ser Glu Thr Ser Leu
    370                 375                 380

Ser Phe Phe Lys Asp Phe Asp Ala Thr Val Lys Ile Gly Ser Tyr Ser
385                 390                 395                 400

Arg Asn Ser Lys Thr Tyr Lys Lys Leu Thr Gln Ser Ile Lys Ser Tyr
                405                 410                 415

Ala Asp Gly Phe Ile Gln Leu Val Gln Tyr Thr Pro Ser Asn Gly
            420                 425                 430

Ser Leu Ala Glu Gln Tyr Asp Arg Asn Thr Ala Ala Pro Leu Ser Ala
        435                 440                 445

Asn Asp Leu Thr Trp Ser Phe Ala Ser Phe Leu Thr Ala Thr Gln Arg
450                 455                 460

Arg Asp Ala Val Val Pro Pro Ser Trp Gly Ala Lys Ser Ala Asn Lys
465                 470                 475                 480

Val Pro Thr Thr Cys Ser Ala Ser Pro Val Val Gly Thr Tyr Lys Ala
                485                 490                 495

Pro Thr Ala Thr Phe Ser Ser Lys Thr Lys Cys Val Pro Ala Lys Asp
            500                 505                 510

Ile Val Pro Ile Thr Phe Tyr Leu Ile Glu Asn Thr Tyr Tyr Gly Glu
        515                 520                 525

Asn Val Phe Met Ser Gly Asn Ile Thr Ala Leu Gly Asn Trp Asp Ala
    530                 535                 540

Lys Lys Gly Phe Pro Leu Thr Ala Asn Leu Tyr Thr Gln Asp Gln Asn
545                 550                 555                 560

Leu Trp Phe Ala Ser Val Glu Phe Ile Pro Ala Gly Thr Pro Phe Glu
                565                 570                 575

Tyr Lys Tyr Tyr Lys Val Glu Pro Asn Gly Asp Ile Thr Trp Glu Lys
            580                 585                 590

Gly Pro Asn Arg Val Phe Val Ala Pro Thr Gly Cys Pro Val Gln Pro
        595                 600                 605

His Ser Asn Asp Val Trp Gln Phe
610                 615

<210> SEQ ID NO 2
<211> LENGTH: 593

```
<212> TYPE: PRT
<213> ORGANISM: Talaromyces emersonii

<400> SEQUENCE: 2

Ala Thr Gly Ser Leu Asp Ser Phe Leu Ala Thr Glu Thr Pro Ile Ala
1               5                   10                  15

Leu Gln Gly Val Leu Asn Asn Ile Gly Pro Asn Gly Ala Asp Val Ala
            20                  25                  30

Gly Ala Ser Ala Gly Ile Val Val Ala Ser Pro Ser Arg Ser Asp Pro
        35                  40                  45

Asn Tyr Phe Tyr Ser Trp Thr Arg Asp Ala Ala Leu Thr Ala Lys Tyr
    50                  55                  60

Leu Val Asp Ala Phe Asn Arg Gly Asn Lys Asp Leu Glu Trp Glu Gln
65                  70                  75                  80

Thr Ile Gln Gln Tyr Ile Ser Ala Gln Ala Lys Val Gln Thr Ile Ser
                85                  90                  95

Asn Pro Ser Gly Asp Leu Ser Thr Gly Gly Leu Gly Glu Pro Lys Phe
            100                 105                 110

Asn Val Asn Glu Thr Ala Phe Thr Gly Pro Trp Gly Arg Pro Gln Arg
        115                 120                 125

Asp Gly Pro Ala Leu Arg Ala Thr Ala Leu Ile Ala Tyr Ala Asn Tyr
    130                 135                 140

Leu Ile Asp Asn Gly Glu Ala Ser Thr Ala Asp Glu Ile Ile Trp Pro
145                 150                 155                 160

Ile Val Gln Asn Asp Leu Ser Tyr Ile Thr Gln Tyr Trp Asn Ser Ser
                165                 170                 175

Thr Phe Asp Leu Trp Glu Glu Val Glu Gly Ser Ser Phe Phe Thr Thr
            180                 185                 190

Ala Val Gln His Arg Ala Leu Val Glu Gly Asn Ala Leu Ala Thr Arg
        195                 200                 205

Leu Asn His Thr Cys Ser Asn Cys Val Ser Gln Ala Pro Gln Val Leu
    210                 215                 220

Cys Phe Leu Gln Ser Tyr Trp Thr Gly Ser Tyr Val Leu Ala Asn Phe
225                 230                 235                 240

Gly Gly Ser Gly Arg Ser Gly Lys Asp Val Asn Ser Ile Leu Gly Ser
                245                 250                 255

Ile His Thr Phe Asp Pro Ala Gly Gly Cys Asp Asp Ser Thr Phe Gln
            260                 265                 270

Pro Cys Ser Ala Arg Ala Leu Ala Asn His Lys Val Val Thr Asp Ser
        275                 280                 285

Phe Arg Ser Ile Tyr Ala Ile Asn Ser Gly Ile Ala Glu Gly Ser Ala
    290                 295                 300

Val Ala Val Gly Arg Tyr Pro Glu Asp Val Tyr Gln Gly Gly Asn Pro
305                 310                 315                 320

Trp Tyr Leu Ala Thr Ala Ala Ala Glu Gln Leu Tyr Asp Ala Ile
                325                 330                 335

Tyr Gln Trp Lys Lys Ile Gly Ser Ile Ser Ile Thr Asp Val Ser Leu
                340                 345                 350

Pro Phe Phe Gln Asp Ile Tyr Pro Ser Ala Ala Val Gly Thr Tyr Asn
            355                 360                 365

Ser Gly Ser Thr Thr Phe Asn Asp Ile Ile Ser Ala Val Gln Thr Tyr
    370                 375                 380

Gly Asp Gly Tyr Leu Ser Ile Val Glu Lys Tyr Thr Pro Ser Asp Gly
385                 390                 395                 400
```

```
Ser Leu Thr Glu Gln Phe Ser Arg Thr Asp Gly Thr Pro Leu Ser Ala
                405                 410                 415

Ser Ala Leu Thr Trp Ser Tyr Ala Ser Leu Leu Thr Ala Ser Ala Arg
            420                 425                 430

Arg Gln Ser Val Val Pro Ala Ser Trp Gly Glu Ser Ser Ala Ser Ser
        435                 440                 445

Val Leu Ala Val Cys Ser Ala Thr Ser Ala Thr Gly Pro Tyr Ser Thr
450                 455                 460

Ala Thr Asn Thr Val Trp Pro Ser Ser Gly Ser Gly Ser Ser Thr Thr
465                 470                 475                 480

Thr Ser Ser Ala Pro Cys Thr Thr Pro Thr Ser Val Ala Val Thr Phe
                485                 490                 495

Asp Glu Ile Val Ser Thr Ser Tyr Gly Glu Thr Ile Tyr Leu Ala Gly
            500                 505                 510

Ser Ile Pro Glu Leu Gly Asn Trp Ser Thr Ala Ser Ala Ile Pro Leu
        515                 520                 525

Arg Ala Asp Ala Tyr Thr Asn Ser Asn Pro Leu Trp Tyr Val Thr Val
530                 535                 540

Asn Leu Pro Pro Gly Thr Ser Phe Glu Tyr Lys Phe Phe Lys Asn Gln
545                 550                 555                 560

Thr Asp Gly Thr Ile Val Trp Glu Asp Pro Asn Arg Ser Tyr Thr
                565                 570                 575

Val Pro Ala Tyr Cys Gly Gln Thr Thr Ala Ile Leu Asp Asp Ser Trp
            580                 585                 590

Gln

<210> SEQ ID NO 3
<211> LENGTH: 640
<212> TYPE: PRT
<213> ORGANISM: Aspergillus niger

<400> SEQUENCE: 3

Met Ser Phe Arg Ser Leu Leu Ala Leu Ser Gly Leu Val Cys Thr Gly
1               5                   10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175
```

```
Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
                260                 265                 270

Leu Leu Gly Ser Ile His Thr Phe Asp Pro Glu Ala Ala Cys Asp Asp
            275                 280                 285

Ser Thr Phe Gln Pro Cys Ser Pro Arg Ala Leu Ala Asn His Lys Glu
        290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
                340                 345                 350

Tyr Asp Ala Leu Tyr Gln Trp Asp Lys Gln Gly Ser Leu Glu Val Thr
            355                 360                 365

Asp Val Ser Leu Asp Phe Phe Lys Ala Leu Tyr Ser Asp Ala Ala Thr
        370                 375                 380

Gly Thr Tyr Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
        435                 440                 445

Ala Asn Asn Arg Arg Asn Ser Val Val Pro Ala Ser Trp Gly Glu Thr
450                 455                 460

Ser Ala Ser Ser Val Pro Gly Thr Cys Ala Thr Ser Ala Ile Gly
465                 470                 475                 480

Thr Tyr Ser Ser Val Thr Val Thr Ser Trp Pro Ser Ile Val Ala Thr
            485                 490                 495

Gly Gly Thr Thr Thr Thr Ala Thr Pro Thr Gly Ser Gly Ser Val Thr
        500                 505                 510

Ser Thr Ser Lys Thr Thr Ala Thr Ala Ser Lys Thr Ser Thr Ser Thr
        515                 520                 525

Ser Ser Thr Ser Cys Thr Thr Pro Thr Ala Val Ala Val Thr Phe Asp
        530                 535                 540

Leu Thr Ala Thr Thr Thr Tyr Gly Glu Asn Ile Tyr Leu Val Gly Ser
545                 550                 555                 560

Ile Ser Gln Leu Gly Asp Trp Glu Thr Ser Asp Gly Ile Ala Leu Ser
                565                 570                 575

Ala Asp Lys Tyr Thr Ser Ser Asp Pro Leu Trp Tyr Val Thr Val Thr
            580                 585                 590
```

-continued

Leu Pro Ala Gly Glu Ser Phe Glu Tyr Lys Phe Ile Arg Ile Glu Ser
          595                 600                 605

Asp Asp Ser Val Glu Trp Glu Ser Asp Pro Asn Arg Glu Tyr Thr Val
610                 615                 620

Pro Gln Ala Cys Gly Thr Ser Thr Ala Thr Val Thr Asp Thr Trp Arg
625                 630                 635                 640

<210> SEQ ID NO 4
<211> LENGTH: 556
<212> TYPE: PRT
<213> ORGANISM: Trametes cingulata

<400> SEQUENCE: 4

Gln Ser Ser Ala Ala Asp Ala Tyr Val Ala Ser Glu Ser Pro Ile Ala
1               5                   10                  15

Lys Ala Gly Val Leu Ala Asn Ile Gly Pro Ser Gly Ser Lys Ser Asn
            20                  25                  30

Gly Ala Lys Ala Gly Ile Val Ile Ala Ser Pro Ser Thr Ser Asn Pro
        35                  40                  45

Asn Tyr Leu Tyr Thr Trp Thr Arg Asp Ser Ser Leu Val Phe Lys Ala
50                  55                  60

Leu Ile Asp Gln Phe Thr Thr Gly Glu Asp Thr Ser Leu Arg Thr Leu
65                  70                  75                  80

Ile Asp Glu Phe Thr Ser Ala Glu Ala Ile Leu Gln Gln Val Pro Asn
                85                  90                  95

Pro Ser Gly Thr Val Ser Thr Gly Gly Leu Gly Glu Pro Lys Phe Asn
            100                 105                 110

Ile Asp Glu Thr Ala Phe Thr Asp Ala Trp Gly Arg Pro Gln Arg Asp
        115                 120                 125

Gly Pro Ala Leu Arg Ala Thr Ala Ile Ile Thr Tyr Ala Asn Trp Leu
    130                 135                 140

Leu Asp Asn Lys Asn Thr Thr Tyr Val Thr Asn Thr Leu Trp Pro Ile
145                 150                 155                 160

Ile Lys Leu Asp Leu Asp Tyr Val Ala Ser Asn Trp Asn Gln Ser Thr
                165                 170                 175

Phe Asp Leu Trp Glu Glu Ile Asn Ser Ser Phe Phe Thr Thr Ala
            180                 185                 190

Val Gln His Arg Ala Leu Arg Glu Gly Ala Thr Phe Ala Asn Arg Ile
        195                 200                 205

Gly Gln Thr Ser Val Val Ser Gly Tyr Thr Thr Gln Ala Asn Asn Leu
    210                 215                 220

Leu Cys Phe Leu Gln Ser Tyr Trp Asn Pro Thr Gly Gly Tyr Ile Thr
225                 230                 235                 240

Ala Asn Thr Gly Gly Arg Ser Gly Lys Asp Ala Asn Thr Val Leu
                245                 250                 255

Thr Ser Ile His Thr Phe Asp Pro Ala Ala Gly Cys Asp Ala Val Thr
            260                 265                 270

Phe Gln Pro Cys Ser Asp Lys Ala Leu Ser Asn Leu Lys Val Tyr Val
        275                 280                 285

Asp Ala Phe Arg Ser Ile Tyr Ser Ile Asn Ser Gly Ile Ala Ser Asn
    290                 295                 300

Ala Ala Val Ala Thr Gly Arg Tyr Pro Glu Asp Ser Tyr Met Gly Gly
305                 310                 315                 320

Asn Pro Trp Tyr Leu Thr Thr Ser Ala Val Ala Glu Gln Leu Tyr Asp
                325                 330                 335

```
Ala Leu Ile Val Trp Asn Lys Leu Gly Ala Leu Asn Val Thr Ser Thr
            340             345             350

Ser Leu Pro Phe Phe Gln Gln Phe Ser Ser Gly Val Thr Val Gly Thr
        355             360             365

Tyr Ala Ser Ser Ser Ser Thr Phe Lys Thr Leu Thr Ser Ala Ile Lys
    370             375             380

Thr Phe Ala Asp Gly Phe Leu Ala Val Asn Ala Lys Tyr Thr Pro Ser
385             390             395             400

Asn Gly Gly Leu Ala Glu Gln Tyr Ser Arg Ser Asn Gly Ser Pro Val
            405             410             415

Ser Ala Val Asp Leu Thr Trp Ser Tyr Ala Ala Ala Leu Thr Ser Phe
            420             425             430

Ala Ala Arg Ser Gly Lys Thr Tyr Ala Ser Trp Gly Ala Ala Gly Leu
            435             440             445

Thr Val Pro Thr Thr Cys Ser Gly Ser Gly Gly Ala Gly Thr Val Ala
            450             455             460

Val Thr Phe Asn Val Gln Ala Thr Thr Val Phe Gly Glu Asn Ile Tyr
465             470             475             480

Ile Thr Gly Ser Val Pro Ala Leu Gln Asn Trp Ser Pro Asp Asn Ala
            485             490             495

Leu Ile Leu Ser Ala Ala Asn Tyr Pro Thr Trp Ser Ser Thr Val Asn
            500             505             510

Leu Pro Ala Ser Thr Thr Ile Glu Tyr Lys Tyr Ile Arg Lys Phe Asn
            515             520             525

Gly Ala Val Thr Trp Glu Ser Asp Pro Asn Asn Ser Ile Thr Thr Pro
            530             535             540

Ala Ser Gly Thr Phe Thr Gln Asn Asp Thr Trp Arg
545             550             555
```

METHOD FOR PRODUCTION OF BREWERS WORT

CROSS-REFERENCE TO RELATED APPLICATIONS

This application is a 35 U.S.C. 371 national application of PCT/EP2012/056568 filed Apr. 11, 2012 which claims priority or the benefit under 35 U.S.C. 119 of European application no. 11162594.3 filed Apr. 15, 2011 and U.S. provisional application No. 61/475,762 filed Apr. 15, 2011 the contents of which are fully incorporated herein by reference.

REFERENCE TO A SEQUENCE LISTING

This application contains a Sequence Listing in computer readable form. The computer readable form is incorporated herein by reference.

FIELD OF INVENTION

The present invention in general relates to method for production of brewers wort. Particularly the present invention relates to a method for production of brewers wort by adding a certain glucoamylase.

BACKGROUND OF THE INVENTION

In modern mashing processes, enzymes are often added as a supplement when mashing malt is low in enzymes or to allow use of all adjunct grists. Enzymes may also be applied in mashing of well modified malts with high enzyme content in order to increase the extract recovery as well as the amount of fermentable sugars. The enzymes used include amylase, glucoamylase, pullulanase etc.

U.S. Pat. No. 3,379,534 describes preparation of a low dextrin beer by using amyloglucosidase.

U.S. Pat. No. 4,536,477 describes a thermostable glucoamylase especially useful for preparation of glucose containing syrups from starch.

WO 2009/075682 describes the use of a certain pullulanase to produce a brewers wort where mashing is achieved using a smaller amount of enzyme protein.

Matthews et al., 2001, Journal of Institute of brewing 107(3) pp 185-194 discloses preparation of a low carbohydrate beer by mashing at high temperature with glucoamylase, which is derived from *Aspergillus niger*.

There stills exists need for methods that would help reduce mashing time and increase sugar profile in the production of brewers wort.

SUMMARY OF THE INVENTION

The present inventors have surprisingly found that by use of a particular glucoamylase, mashing can be achieved using a lower enzyme dosage, the mashing process time can be shortened and also the sugar profile of the wort can be improved.

Accordingly in one aspect, the invention relates to a method of producing a brewer's wort comprising adding to a mash, a glucoamylase that is active during mashing conditions at temperatures of at least 65° C.

In another aspect, the invention relates to a method of producing a brewer's wort comprising adding to a mash, a glucoamylase that is still active during lautering and has at least 10% residual activity at 80° C.

In one aspect, the residual activity is measured at pH 6.0 and by the formation of glucose using maltodextrin as a substrate.

Accordingly, in another aspect, the invention relates to a method for production of a brewer's wort comprising adding to a mash, a glucoamylase that is at least 50% identical to the sequence shown in SEQ ID NO: 1.

In one aspect, mashing process of the method includes a step of incubation of at least 65° C. for at least 20 minutes.

In one aspect, the glucoamylase is active under lautering.

In another aspect, the glucoamylase is active under mashing-off.

In another aspect, the method further comprises adding a pullulanase.

In another aspect, the method further comprises adding a protease.

In another aspect, the method further comprises adding a xylanase.

In another aspect, the method further comprises adding a lipase.

In another aspect, the method further comprises adding a cellulase.

In another aspect, the method further comprises adding an amylase.

In another aspect, the method further comprises adding a beta glucanase.

In one aspect, the glucoamylase is introduced at the beginning of mashing.

In another aspect, the glucoamylase is introduced during mashing.

In one aspect, the glucoamylase is introduced under lautering.

In another aspect, the glucoamylase addition is done at a temperature between 65° C. and 90° C.

In one aspect, practicing the method of the invention results in a wort which has more than 80%, glucose, compared to the total carbohydrate content of the wort.

In one aspect, the concentration of glucoamylase is about 0.0005 to about 200 mg of enzyme protein (EP) per g of total weight of the grist.

In one aspect, the mash is made of grist comprising malted and/or unmalted grain.

In one aspect, the glucoamylase is obtained from *Penicillium*.

In another aspect, the glucoamylase is obtained from *Penicillium oxalicum*.

In one aspect, the wort is further fermented to obtain an alcoholic beverage.

In another aspect, the alcoholic beverage is beer.

In one aspect, the invention is related to the use of glucoamylase having at least 50% identity to the sequence shown in SEQ ID NO: 1 for the production of a brewer's wort.

DETAILED DESCRIPTION OF THE INVENTION

Brewing processes are well-known in the art, and generally involve the steps of malting, mashing, and fermentation. Mashing is the process of converting starch from the milled barley malt and solid adjuncts into fermentable and unfermentable sugars to produce wort of the desired composition. Traditional mashing involves mixing milled barley malt and adjuncts with water at a set temperature and volume to continue the biochemical changes initiated during the malting process. The mashing process is conducted over a period of time at various temperatures in order to activate the endogenous enzymes responsible for the degradation of proteins and carbohydrates. By far the most important change brought about in mashing is the conversion of starch molecules into fermentable sugars. The principal enzymes responsible for starch conversion in a traditional mashing process are alpha-amylases, beta-amylases and dextranases. Alpha-amylase very rapidly reduces insoluble and soluble starch by splitting starch molecules into many shorter chains that can be attacked by beta-amylase. The disaccharide produced is maltose. In addition to the maltose formed during mashing short branched glucose oligomers are produced. The short branched glucose oligomers are non fermentable sugars and add to the taste as well as the amount of calories of the finished beer. After mashing, when all the starch has been broken down, it is necessary to separate the liquid extract (the wort) from the solids (spent grains). Wort separation, lautering, is important because the solids contain large amounts of protein, poorly modified starch, fatty material, silicates, and polyphenols (tannins). Prior to lautering, the mash temperature may be raised to about 75-78° C. (165-173° F.) (known as mashing-off). Following the separation of the wort from the spent grains, the wort may be fermented with brewer's yeast to produce a beer. The extract retained in the spent grain after collection of the first wort may also be washed out by adding hot water on top of the lauter cake. This process is called sparging. The hot water flows through the spent grain and dissolves the remaining extract. The diluted wort is called second wort and its extract decreases from the original gravity of the first wort down to 1-2%. After addition of hops, the wort is boiled. Hereby numerous substances including several proteins are denatured and a precipitation of polyphenols will take place. After cooling and removal of precipitates, the finished beer wort (a) is aerated and yeast is added. After a main fermentation, lasting typically 5-10 days, most of the yeast is removed and the so-called green beer (b) is stored at a low temperature, typically at 0-5° C. for 1 to 12 weeks. During this period the remaining yeast will precipitate together with polyphenols. To remove the remaining excess polyphenols a filtration is performed. The fermented beer (c) may now be carbonized prior to bottling. Carbon dioxide not only contributes to the perceived "fullness" or "body" and as a flavor enhancer, it also acts as an enhancer of the foaming potential and plays an important role in extending the shelf life of the product. Further information on conventional brewing processes may be found in "Technology Brewing and Malting" by Wolfgang Kunze of the Research and Teaching Institute of Brewing, Berlin (VLB), 2nd revised Edition 1999, ISBN 3-921690-39-0.

The short branched glucose oligomers formed during mashing may be further hydrolyzed by addition of exogenous enzymes (enzymes added in addition to the malt). Debranching enzymes such as pullulanase and isoamylase hydrolyze the branching alpha-1-6 glucosidic bonds in during the starch degradation, thereby facilitation a higher level of hydrolysis by beta-amylase and glucoamylases, leading to higher levels of maltose and glucose and less unfermentable dextrins.

In one aspect, the present invention provides a method to produce low carbohydrate content (low carb) beers. A typical wort consists of a mixture of starch derived carbohydrates which are classified as fermentable or non-fermentable according to whether they can be converted into ethanol by brewer's yeast. In traditional mashing the fermentable carbohydrates are formed by hydrolysis of grain starch by malt alpha- and beta-amylases. Starch is a glucose polymer in which the glucose residues are linked by either alpha-1,4 bonds or alpha-1,6 bonds. During the mashing cycle the starch is first solubilized and then a portion of the starch molecules are hydrolyzed into non-fermentable dextrins and to low molecular weight sugars, such as glucose, maltose and maltotriose, which brewer's yeast can ferment into ethanol. The non-fermentable or limit dextrin fraction consists of all sugars with a higher degree of polymerisation (DP) than maltotriose. The composition of the wort can vary depending on the starting material, mash cycles and other variables. The carbohydrate composition of a typical wort consists of 65-80% fermentable sugars, and 20-35% non-fermentable limit dextrins. During fermentation the fermentable fraction is converted into ethanol to a final concentration of 3 to 6% w/w. The limit dextrins are not converted into ethanol and remains in the final beer adding to the carbohydrate content of the beverage. In the production of "low carb" or super attenuated beers, an attempt is made to obtain a higher proportion of alcohol and a lower amount of residual dextrin. Glucoamylases are often used in brewing to reduce the content of limit dextrins. However, as glucoamylases are much more efficient in hydrolyzing the alpha-1, 4 bonds and have difficulties in hydrolyzing the alpha-1,6 bonds, they are normally used in very high concentrations.

In one aspect, the present invention provides a method suitable for producing a wort that is low in non-fermentable sugars. In another aspect, the invention relates to a method for producing a wort that is enriched in glucose. In another aspect, the invention relates to a method for producing a wort that is depleted in maltose. The method applies an expressly selected glucoamylase activity.

The inventors have surprisingly found that using glucoamylases which are active at much higher temperatures than glucoamylases normally used in brewing can provide many advantages. For example, by applying glucoamylases active at lautering, the inventors found that they can benefit from not only the traditional saccharification step but also during the rest of the lautering process. This therefore reduced the amount of glucoamylase to reach the same RDF (Real Degree of Fermentation). Alternatively using the method of the invention, one can even obtain higher RDF values and/or one can reduce the saccharification time at 60-64° C. The inventors also found that having a glucoamylase active at higher temperature enabled mashing in of adjuncts where the starch has a high gelatinization temperature, such as corn, rice and sorghum. A high level of starch hydrolysis of such adjuncts will be ensured as the glucoamylase is active when the starch is gelatinized, The inventors also found that further efficiency will be obtained by addition of a pullulanase, and using a holding step during mashing where the starch of the adjuncts are gelatinized and where with the pullulanase and the glucoamylase is active.

Definitions

Throughout this disclosure, various terms that are generally understood by those of ordinary skill in the arts are used. Several terms are used with specific meaning, however, and are meant as defined by the following.

As used herein the term "grist" is understood as the starch or sugar containing material that is the basis for beer production, e.g. the barley malt and the adjunct. Generally, the grist does not contain any added water.

The term "malt" is understood as any malted cereal grain, in particular barley.

The term "adjunct" is understood as the part of the grist which is not barley malt. The adjunct may be any starch rich plant material e.g. unmalted grain, such as, but not limited to, barley, corn, rice, sorghum, and wheat and also includes readily fermentable sugar and/or syrup. The starch of some of the adjuncts has a relatively low gelatinization temperature which enable them to be mashed in together with the malt, whereas other adjuncts such as rice, corn and sorghum has a higher gelatinization temperature, such adjuncts are typically separately cooked and liquefied with an alpha-amylase before they are added to the mash The term "mash" is understood as a starch containing slurry comprising crushed barley malt, crushed unmalted grain, other starch containing material, or a combination hereof, steeped in water to make wort.

The term "wort" is understood as the unfermented liquor run-off following extracting the grist during mashing.

The term "spent grains" is understood as the drained solids remaining when the grist has been extracted and the wort separated.

The term "beer" is here understood as fermented wort, i.e. an alcoholic beverage brewed from barley malt, optionally adjunct and hops. The term "beer" as used herein is intended to cover at least beer prepared from mashes prepared from unmalted cereals as well as all mashes prepared from malted cereals, and all mashes prepared from a mixture of malted and unmalted cereals. The term "beer" also covers beers prepared with adjuncts, and beers with all possible alcohol contents.

The term "starch gelatinization" is understood as the irreversible order-disorder transition that starch undergoes when heated in the presence of water. Differential Scanning calorimetry (DSC) in one technique that can be employed to study the gradual process of starch gelatinization describing the onset and peak temperature ($T_o$ & $T_p$) of starch gelatinization. The term "onset gelatinization temperature ($T_o$)" is understood as the temperature at which the gelatinization begins. The term "peak gelatinization temperature ($T_p$)" is understood as the temperature at endotherm peak. The term "conclusion gelatinization temperature ($T_c$)" is understood as the temperature at which the gelatinization has terminated.

Sequence Identity: The relatedness between two amino acid sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment–
Total Number of Gaps in Alignment)

Wort Production

Accordingly in one aspect, the invention relates to a method of producing a brewer's wort comprising adding to a mash, a glucoamylase that is active during mashing conditions at temperatures of at least 65° C.

In another aspect, the invention relates to a method of producing a brewer's wort comprising adding to a mash, a glucoamylase that is still active during lautering and has at least 10% residual activity at 80° C.

In one aspect, the residual activity is measured at pH 6.0 and by the formation of glucose using maltodextrin as a substrate.

In one aspect, the present invention relates to a method for production of brewers wort. Particularly, the present invention relates to a method for production of a brewer's wort comprising adding to a mash, a glucoamylase that is at least 50% identical to the sequence shown in SEQ ID NO: 1.

In accordance with one aspect the mash is obtainable by grounding a grist comprising malt and/or adjunct. Water may preferably be added to the grist, be preheated in order for the mash to attain the desired mash temperature at the moment of mash forming. If the temperature of the formed mash is below the desired mashing temperature, additional heat is preferably supplied in order to attain the desired process temperature. Preferably, the desired mashing temperature is attained within 15 minutes, or more preferably within 10 minutes, such as within 9, 8, 7, 6, 5, 4, 3, 2 minutes or even more preferably within 1 minute after the mash forming, or most preferably the desired mashing temperature is attained at the mash forming. The temperature profile of the mashing process may be a profile from a conventional mashing process wherein the temperatures are set to achieve optimal degradation of the grist dry matter by the malt enzymes.

The mashing process generally applies a controlled stepwise increase in temperature, where each step favors one enzymatic action over the other, eventually degrading proteins, cell walls and starch. Mashing temperature profiles are generally known in the art. In the present invention the saccharification (starch degradation) step in the mashing process is preferably performed between 60° C. and 66° C., more preferably between 61° C. and 65° C., even more preferably between 62° C. and 64° C., and most preferably between 63° C. and 64° C. In a particular embodiment of the present invention the saccharification temperature is 64° C.

In one aspect, the invention relates to a method of producing a brewer's wort comprising adding to a mash, a glucoamylase that is active during mashing conditions at temperatures of at least 65° C. In another aspect, the glucoamylase is active during mashing conditions at at least 68° C., e.g., 70° C., e.g., 72° C., for e.g. 75° C., for e.g. 76° C., e.g., 77° C., e.g., 78° C., e.g., 79° C., e.g., 80° C.

In one aspect, the invention the glucoamylase is active during lautering and/or mash filtration.

In one aspect, the mashing process of the present invention includes but not limited to a mashing-off step. In one aspect, the mashing-off step includes but not limited to incubation of the mash at a temperature of at least 65° C. for at least 20 minutes. In one aspect, the mashing-off step comprises incubation of the mash at a temperature of at least 65° C., e.g., at least 66° C., at least 67° C., at least 68° C., at least 69° C., at least 70° C., at least 71° C., at least 72° C., at least 73° C., at least 74° C. or at least 75° C., at least 76° C., at least 77° C., at least 78° C., at least 79° C., at least 80° C., at least 81° C., at least 82° C., at least 83° C., at least 84° C. or at least 85° C. for at least 20 minutes e.g., at least 25 minutes, at least 30 minutes, at least 35 minutes, at least 40 minutes, at least 45 minutes, at least 50 minutes, at least 55 minutes, at least 60 minutes, at least 65 minutes, at least 70 minutes, at least 75 minutes, at least 80 minutes, at least 85 minutes, at least 90 minutes, at least 95 minutes, at least 100 minutes, at least 105 minutes, at least 110 minutes, at least 115 minutes, at least 120 minutes, at least 125 minutes, at least 130 minutes, at least 135 minutes, at least 140 minutes, at least 145 minutes such as at least 150 minutes. In a particular embodiment the mashing-off is done at 75° C. for 120 minutes.

In one aspect, the pH of the mash is in the range of about 4.6 to about 6.4. In another aspect, the pH is in the range of about 4.6 to 6.2, such as in the range between pH about 4.8 to about 6.0, preferably in the range between pH about 5.0 to about 6.0, more preferably in the range between pH about 5.0 to about 5.6, even more preferably in the range between pH about 5.0 to about 5.4.

The malt is preferably derived from one or more of the grains selected from the list consisting of corn, barley, wheat, rye, sorghum, millet and rice. Preferably, the malt is barley malt. The grist preferably comprises from 0.5% to 99%, preferably from 1% to 95%, more preferably from 5% to 90%, even more preferably from 10% to 80% malt.

In addition to malted grain, the grist may preferably comprise adjunct such as unmalted corn, or other unmalted grain, such as barley, wheat, rye, oat, corn, rice, milo, millet and/or sorghum, or raw and/or refined starch and/or sugar containing material derived from plants like wheat, rye, oat, corn, rice, milo, millet, sorghum, potato, sweet potato, cassava, tapioca, sago, banana, sugar beet and/or sugar cane. For the invention, adjuncts may be obtained from tubers, roots, stems, leaves, legumes, cereals and/or whole grain. Preferred is adjunct obtained from corn and/or rice, more preferred the adjunct is rice starch, corn starch and/or corn grits. The mash preferably comprises from 1% to 60%, preferably from 5% to 45%, more preferably from 10% to 40% adjunct starch. Adjunct may also comprise readily fermentable carbohydrates such as sugars or syrups and may be added to the malt mash before, during or after the mashing process of the invention but is preferably added after the mashing process. Prior to forming the mash, the malt and/or adjunct is preferably milled and most preferably dry or wet milled. In one aspect, the adjunct has a high gelatinization temperature, more particularly higher onset gelatinization temperature for e.g. corn, rice and sorghum. In one aspect, the adjunct is gelatinized prior to mashing. In another aspect, the adjunct is not gelatinized prior to mashing.

In one aspect, the mash is comprised of at least 20% of adjuncts which have a starch gelatinization temperature, preferably onset gelatinization temperature, of at least 65° C. In another aspect, the mash is comprised of at least 25%, e.g. at least 30%, at least 35%, at least 40%, at least 45%, at least 50%, at least 55%, at least 60% such as at least 65% adjuncts which have a starch gelatinization temperature, preferably onset gelatinization temperature, of at least 65° C.

In one aspect, the mash comprises at least 10% unmalted grains compared to the total grist. In another aspect, the mash comprises at least 15%, e.g. at least 20%, at least 25%, at least 30%, at least 35%, at least 40%, at least 45%, at least 50%, at least 55%, such as at least 60% unmalted grains.

In one aspect of the invention, the adjunct comprises corn. In another aspect of the invention, the mash comprises at least 20% of corn adjunct. In one aspect, the mash comprises at least 25%, e.g., at least 30%, at least 35%, at least 40%, at least 45%, at least 50%, at least 55%, such as at least 60% of corn adjunct.

In one aspect, the corn adjunct is ungelatinized when added to the mash.

In one aspect of the invention, the adjunct comprises rice. In another aspect of the invention, the mash comprises at least 20% of rice adjunct. In one aspect, the mash comprises at least 25%, e.g., at least 30%, at least 35%, at least 40%, at least 45%, at least 50%, at least 55%, such as at least 60% of rice adjunct.

In one aspect, the rice adjunct is ungelatinized when added to the mash.

In one aspect, the glucoamylase is exogenously supplied and/or present in the mash. In one aspect, the glucoamylase is introduced at the beginning of mashing. In another aspect, the glucoamylase is introduced during mashing. In another aspect, the glucoamylase is introduced under lautering.

In another preferred embodiment, a further enzyme(s) is added to the mash, said enzyme(s) including but not limited to alpha amylase, isoamylase, protease, cellulase, glucanase, laccase, xylanase, lipase, phospholipase, phytase, phytin and esterase.

In one aspect of the method the further enzyme added includes but is not limited to a pullulanase.

In one aspect of the method the further enzyme added includes but is not limited to an amylase, preferably but not limited to an alpha amylase.

In one aspect of the method the further enzyme added includes but is not limited to a protease.

In one aspect of the method the further enzyme added includes but is not limited to a cellulase.

In one aspect of the method the further enzyme added includes but is not limited to a xylanase.

In one aspect of the method the further enzyme added includes but is not limited to a lipase.

In one aspect of the method the further enzyme added includes but is not limited to a glucanase, preferably but not limited to beta glucanase.

In one aspect, practicing the method of the invention leads to increased levels of glucose in the wort. In one aspect, the increase in glucose is at least 1% e.g., at least 2%, at least 3%, at least 4%, at least 5%, at least 6%, at least 7%, at least 8%, at least 9%, at least 10% when compared to the wort produced in the absence of the such a glucoamylase.

In one aspect, practising the method of the invention leads to a wort which has at least 80% glucose when compared to the total carbohydrate content of the wort. In another aspect, the wort has at least 81% glucose, e.g., at least 82%, at least 83%, at least 84%, at least 85%, at least 86%, at least 87%, at least 88%, at least 89%, at least 90%, at least 91%, at least 92%, at least 92.5%, at least 93%, at least 93.5%, such as at least 94% glucose when compared to the total carbohydrate content of the wort.

In one aspect, the mash and/or the wort comprise no added glucose syrup.

In another aspect, practicing the method of the invention leads to additional glucose formation at temperatures between 65° C. to 90° C. In one aspect, the additional glucose formed at temperatures between 65° C. to 90° C. is at least 1% e.g., at least 2%, at least 3%, at least 4%, at least 5%, at least 6%, at least 7%, at least 8%, at least 9%, at least 10% when compared to the wort produced in the absence of the such a glucoamylase.

In one aspect, practicing the method of the invention leads to decreased concentration of maltose in the wort. In one aspect, the concentration of maltose is decreased by at least 0.5%, e.g., at least 1% e.g., at least 2%, at least 3%, at least 4%, at least 5%, when compared to the wort produced in the absence of such a glucoamylase.

In one aspect, practicing the method of the invention leads to increased concentration of glucose and decreased concentration of maltose in the wort. In one aspect, the concentration of glucose is increased by at least 1% e.g., at least 2%, at least 3%, at least 4%, at least 5%, at least 6%, at least 7%, at least 8%, at least 9%, at least 10% and the concentration of maltose is decreased by at least 0.5%, e.g., at least 1% e.g., at least 2%, at least 3%, at least 4%, at least 5%, when compared to the wort produced in the absence of the such a glucoamylase.

In one aspect, the method of the invention leads to shortened mashing times. In one aspect, the method leads to decrease in mashing time by at least 5 minutes e.g., at least 10 minutes, at least 15 minutes, at least 20 minutes, at least 25 minutes more preferably by at least 30 minutes compared to the method done in the absence of such a glucoamylase.

In one aspect, the method of the invention leads to mashing times that are below 120 minutes. In another aspect, the mashing time is below 110 minutes, e.g. below 100 minutes, such as e.g., below 90 minutes, below 80 minutes, below 70 minutes, below 60 minutes, below 50 minutes, e.g., below 40 minutes.

In one aspect, the method of the invention leads to lower saccharification times, i.e. the time during mashing where the temperature is between 60° C. and 66° C. In one aspect, the time is less than 60 minutes. In another aspect, the time is less than 58 minutes, e.g., less than 56 minutes, less than 54 minutes, less than 52 minutes, less than 50 minutes, less than 48 minutes, less than 46 minutes, less than 44 minutes, less than 42 minutes, less than 40 minutes, less than 38 minutes, less than 36 minutes, less than 34 minutes, less than 32 minutes, less than 30 minutes, less than 28 minutes, less than 26 minutes, less than 24 minutes, less than 22 minutes, such as less than 20 minutes.

In another aspect, the method of the invention leads to lower enzyme dosage, particularly the glucoamylase dosage. In one aspect, the glucoamylase dosage is reduced by at least 10% e.g. at least 15%, at least 20%, at least 25%, at least 30%, at least 35%, at least 40%, at least 45%, at least 50%, at least 55%, at least 60%, at least 65%, at least 70%, such as at least 75% when compared to a method done with a glucoamylase found in the prior art.

During the mashing process, starch extracted from the grist is gradually hydrolyzed into fermentable sugars and smaller dextrins. Preferably, the mash is starch negative to iodine testing, before extracting the wort.

Obtaining the wort from the mash typically includes straining the wort from the spent grains, i.e., the insoluble grain and husk material forming part of grist. Hot water may be run through the spent grains to rinse out, or sparge, any remaining extract from the grist. Optionally the application of a thermostable cellulase in the process of the present invention results in efficient reduction of beta-glucan level facilitating wort straining thus ensuring reduced cycle time and high extract recovery. Preferably the extract recovery is at least 80%, preferably at least 81%, more preferably at least 82%, even more preferably at least 83%, such as at least 84%, at least 85%, at least 86%, at least 87%, at least 88%, at least 89%, at least 90%, and most preferably at least 91%.

Following the separation of the wort from the spent grains of the grist, the wort may be used as it is or it may be dewatered to provide a concentrated and/or dried wort. The concentrated and/or dried wort may be used as brewing extract, as malt extract flavoring, for non-alcoholic malt beverages, malt vinegar, breakfast cereals, for confectionary etc. In a preferred embodiment, the wort is fermented to produce an alcoholic beverage, preferably a beer, e.g., ale, strong ale, bitter, stout, porter, lager, export beer, malt liquor, barley wine, happoushu, high-alcohol beer, low-alcohol beer, low-calorie beer or light beer. Fermentation of the wort may include pitching the wort with a yeast slurry comprising fresh yeast, i.e., yeast not previously used for the invention or the yeast may be recycled yeast. The yeast applied may be any yeast suitable for beer brewing, especially yeasts selected from *Saccharomyces* spp. such as *S. cerevisiae* and *S. uvarum*, including natural or artificially produced variants of these organisms. The methods for fermentation of wort for production of beer are well known to the person skilled in the arts.

The process of the invention may include adding silica hydrogel to the fermented wort to increase the colloidal stability of the beer. The processes may further include adding kieselguhr to the fermented wort and filtering to render the beer bright. In one aspect, the invention provides for a beer produced from the wort, such as a beer produced by fermenting the wort to produce a beer. The beer may be any type of beer, e.g., ales, strong ales, stouts, porters, lagers, bitters, export beers, malt liquors, happoushu, high-alcohol beer, low-alcohol beer, low-calorie beer or light beer.

In one aspect, the invention relates to the use of a glucoamylase that has an amino acid sequence which is at least 50% identical to the amino acid sequence shown in SEQ ID NO: 1 in a wort production process.

In one aspect the invention relates to a wort produced by using a method of this invention.

In another aspect, the invention relates to a beer and a method for producing the same using a wort prepared by the method of this invention.

Enzymes:

The enzymes to be applied in the present invention should be selected for their ability to retain sufficient activity at the process temperature of the processes of the invention, as well as for their ability to retain sufficient activity under the moderately acid pH regime in the mash and should be added in effective amounts. The enzymes may be derived from any source, preferably from a plant or algae, and more preferably from a microorganism, such as from bacteria or fungi.

Glucoamylase (EC 3.2.1.3)

Glucoamylases (Glucan 1,4-alpha-glucosidase, EC 3.2.1.3) are enzymes which catalyze the hydrolysis of terminal (1->4)-linked alpha-D-glucose residues successively from non-reducing ends of the chains with release of beta-D-glucose. The glucoamylase is alternatively called by other names e.g., 4-alpha-D-glucan glucohydrolase; e.g. Amyloglucosidase, e.g. Exo-1,4-alpha-glucosidase, e.g. Gamma-amylase; e.g. Lysosomal alpha-glucosidase etc.

Glucoamylase may be obtained from a microorganism or a plant. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

The glucoamylase of the present invention may be of fungal origin. For example, the glucoamylase may be obtained from yeast such as a *Candida, Kluyveromyces, Pichia, Saccharomyces, Schizosaccharomyces*, or *Yarrowia*. Preferably the glucoamylase may be obtained from a filamentous fungi such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromy-*

*ces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having glucoamylase activity.

In another preferred aspect, the glucoamylase is obtained from *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Penicillium thomii, Penicillium oxalicum, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei,* or *Trichoderma viride.*

In a more preferred aspect, the glucoamylase is obtained from *Penicillium oxalicum*. In a most preferred aspect, the glucoamylase is a *Penicillium oxalicum* polypeptide having glucoamylase activity, e.g., the polypeptide comprising SEQ ID NO: 1.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the techniques known in the art, e.g., using the polynucleotide coding for a polypeptide as a probe. Techniques for isolating microorganisms from natural habitats are well known in the art. The polynucleotide may then be obtained by similarly screening a genomic or cDNA library of such a microorganism. Once a polynucleotide encoding a polypeptide has been detected with the probe(s), the polynucleotide can be isolated or cloned by utilizing techniques that are well known to those of ordinary skill in the art (see, e.g., Sambrook et al. (1989) Molecular cloning: A laboratory manual, Cold Spring Harbor lab., Cold Spring Harbor, N.Y.).

In one aspect, the glucoamylase has an amino acid sequence which is at least 50%, e.g. at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or even at least 99% identical to the amino acid sequence shown in SEQ ID NO: 1.

In a preferred embodiment, the glucoamylase has an amino acid sequence which differs by no more than 100 amino acids, preferably by no more than 80 amino acids, more preferred by no more than 50 amino acids, more preferably by no more than 30 amino acids, even more preferably by no more than 20 amino acids, and most preferably by no more than 10 amino acids from the amino acid sequence of SEQ ID NO: 1.

In one aspect, the invention relates to the use of a glucoamylase that has an amino acid sequence which is at least 50% identical e.g. at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or even at least 99% to the amino acid sequence shown in SEQ ID NO: 1 in a wort production process.

In one aspect, the glucoamylase has a temperature optimum of at least 65° C. In another aspect, the temperature optimum is at least 66° C., e.g., at least 67° C. such as at least 68° C., at least 69° C., at least 70° C., at least 71° C., at least 72° C., at least 73° C., at least 74° C., at least 75° C., at least 76° C., at least 77° C., at least 78° C., at least 79° C., such as at least 80° C. determined by the enzyme's ability to release glucose during incubation at 32-85 C at pH 5.0 to 6.0 for 1 hour. In one aspect, the incubation pH is 6.0. In another aspect, the pH is 5.8. In one aspect, the pH is 5.6. In another aspect, the pH is 5.4. In one aspect, the pH is 5.2. In another aspect, the pH is 5.0.

In one embodiment, the glucoamylase has a temperature optimum of around 65-75° C. determined by the enzyme's ability to release glucose during incubation at 32-85° C. at pH 6.0 for 1 hour as described in example no: 1.

In one embodiment, the glucoamylase has a residual activity of at least 10% such as at least 11%, e.g., 12%, e.g., 13%, e.g., 14%, e.g., 15%, e.g., 16%, e.g., 17%, e.g., 18%, e.g., 19%, e.g., 20% such as at least 21%, e.g., 22%, e.g., 23%, e.g., 24%, e.g., 25%, e.g., 26%, e.g., 27%, e.g., 28%, e.g., 29%, e.g., 30%, e.g., 31%, e.g., 32% as determined by the enzyme's ability to release glucose at pH 6.0 measured by the formation of glucose using maltodextrin as a substrate as described in example no: 1.

In one aspect, the glucoamylase is added in a concentration of about 0.0005 to about 200 mg enzyme protein per gram of total grist, preferably about 0.001 to about 100, more preferably about 0.01 to about 50, even more preferably about 0.05 to about 2.0 mg of enzyme protein (EP) per gram of total weight of the grist.

In one aspect, the concentration of glucoamylase added is less than 0.4 mg enzyme protein (EP) per gram of the total grist. In another aspect, the concentration of glucoamylase is less than 0.35, such as less than 0.3, such as less than 0.25, such as less than 0.2 such as less than 0.15 mg enzyme protein (EP) per gram of the total grist.

Pullulanase (EC 3.2.1.41)

Pullulanase (EC 3.2.1.41) catalyze the hydrolysis of (1->6)-alpha-D-glucosidic linkages in pullulan, amylopectin and glycogen, and in the alpha- and beta-limit dextrins of amylopectin and glycogen. These enzymes were formerly EC 3.2.1.69. They are alternatively called Alpha-dextrin endo-1,6-alpha-glucosidase or Amylopectin 6-glucanohydrolase or Debranching enzyme or Limit dextrinase or Pullulan 6-glucanohydrolase.

The pullulanase according to the present invention is preferably pullulanase from e.g. *Pyrococcus* or *Bacillus*, such as *Bacillus acidopullulyticus* e.g. the one described in Kelly et al., 1994, FEMS Microbiol. Letters 115: 97-106, or a pullulanase available from Novozymes A/S as Promozyme 400L. The pullulanase may also be from *Bacillus naganoencis*, or *Bacillus deramificans* e.g. such as derived from *Bacillus deramificans* (U.S. Pat. No. 5,736,375). The pullulanase may also be an engineered pullulanases from, e.g. a *Bacillus* strain.

Other pullulanases may be derived from *Pyrococcus woesei* described in PCT/DK91/00219, or the pullulanase may be derived from *Fervidobacterium* sp. Ven 5 described in PCT/DK92/00079, or the pullulanase may be derived from *Thermococcus celer* described in PCT/DK95/00097, or the pullulanase may be derived from *Pyrodictium abyssei* described in PCT/DK95/00211, or the pullulanase may be derived from *Fervidobactetium pennavorans* described in PCT/DK95/00095, or the pullulanase may be derived from *Desulforococcus mucosus* described in PCT/DK95/00098.

Most preferably the pullulanase is derived from *Bacillus acidopullulyticus*. A preferred pullulanase enzyme to be used in the processes and/or compositions of the invention is a pullulanase having an amino acid sequence which is at least 50%, such as at least 55%, such as at least 60%, such as at least 65%, such as at least 66%, such as at least 70%, such as at least 75%, such as at least 80%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or even 100% identical to the sequence of the pullulanase 3 disclosed in WO2009075682.

The pullulanase may be added in effective amounts well known to the person skilled in the art. In one aspect, the pullulanase is added in dosage of 0.1 to 3 PUN/g DM, such as 0.2 to 2.9, such as 0.3 to 2.8, such as 0.3 to 2.7 such as 0.3 to 2.6 such as 0.3 to 2.5 such as 0.3 to 2.4, such as 0.3 to 2.3, such as 0.3 to 2.2, such as 0.3 to 2.1, such as 0.3 to 2.0, such as 0.3 to 1.9, such as 0.3 to 1.8, such as 0.3 to 1.7, such as 0.3 to 1.6, most preferably pullulanase is added in dosage such as 0.3 to 1.5, preferably 0.4 to 1.4, more preferably 0.5 to 1.3, more preferably 0.6 to 1.2, more preferably 0.7 to 1.1, more preferably 0.8 to 1.0, more preferably 0.9 to 1.0. In a particular embodiment of the invention the enzyme is added in 0.3 PUN/g DM, such as 0.4 PUN/g DM, such as 0.5 PUN/g DM in a particularly preferred embodiment of the invention the enzymes dose is not larger than 1 PUN/g DM.

One pullulanase unit (PUN) is the amount of enzyme which, under standard conditions (i.e. after 30 minutes reaction time at 40° C. and pH 5.0; and with 0.2% pullulan as substrate) hydrolyzes pullulan, liberating reducing carbohydrate with a reducing power equivalent to 1 micromol glucose per minute. Pullulanase activity is by measured by detection of increased reducing sugar capacity (Somogyi-Nelson reaction) in the following conditions: Substrate: 0.2% pullulan, pH 5.0, reaction 20 time 30 minutes. The samples are analyzed by spectrophotometer at OD 520 nm.

In one aspect, the invention of the method comprises both a glucoamylase and a pullulanase.

Alpha-amylase (EC 3.2.1.1)

A particular alpha-amylase enzyme to be used in the processes and/or compositions of the invention may be a *Bacillus* alpha-amylase. Well-known *Bacillus* alpha-amylases include alpha-amylase derived from a strain of *B. licheniformis*, *B. amyloliquefaciens*, and *B. stearothermophilus*. In one aspect of the present invention, a contemplated *Bacillus* alpha-amylase is an alpha-amylase as defined in WO 99/19467 on page 3, line 18 to page 6, line 27. Preferably the α-amylase has at least 50%, more preferably at least 60%, more preferably at least 70%, more preferably at least 80%, preferably at least 85%, more preferably at least 90%, preferably at least 91%, preferably at least 92%, preferably at least 93%, preferably at least 94%, more preferably at least 95%, preferably at least 96%, preferably at least 97%, more preferably at least 98%, and most preferably at least 99% identity to the amino acid sequence shown in the amino acid sequence disclosed as SEQ ID NO: 3 in WO 99/19467 with the mutations: I181*+G182*+N193F. Also contemplated is the amylase Termamyl® SC from Novozymes A/S. Another particular alpha-amylase to be used in the processes of the invention may be any fungal alpha-amylase, e.g., an alpha-amylase derived from a species within *Aspergillus*, and preferably from a strain of *Aspergillus niger*. Especially contemplated are fungal alpha-amylases which exhibit a high identity, i.e., at least 50%, at least 55%, at least 60%, at least 65%, at least 70%, at least 75%, at least 80%, at least 85% or even at least 90% identity to the amino acid sequence shown as SEQ ID NO: 1 in WO 2002/038787.

The amount of alpha amylase to be added depends on various parameters and is generally known to the person skilled in the art. In one aspect, the alpha amylase activity in the mash is 0.1-1.0 KNU/g, more preferably 0.2-0.4 KNU/g, and most preferably 0.25-0.35 KNU/g dry weight cereal(s). One Kilo Novo alpha amylase Unit (KNU) equals 1000 NU. One KNU is defined as the amount of enzyme which, under standard conditions (i.e. at 37° C.+/−0.05; 0.0003 M Ca2+; and pH 5.6) dextrinizes 5.26 g starch dry substance Merck Amylum solubile.

Isoamylase (E.C. 3.2.1.68)

Another enzyme applied in the processes and/or compositions of the invention may be an alternative debranching enzyme, such as an isoamylase (E.C. 3.2.1.68). Isoamylase hydrolyzes alpha-1,6-D-glucosidic branch linkages in amylopectin and beta-limit dextrins and can be distinguished from pullulanases by the inability of isoamylase to attack pullulan, and by the limited action on alpha-limit dextrins. Isoamylase may be added in effective amounts well known to the person skilled in the art.

Protease

Suitable proteases include microbial proteases, such as fungal and bacterial proteases. Preferred proteases are acidic proteases, i.e., proteases characterized by the ability to hydrolyze proteins under acidic conditions below pH 7. The proteases are responsible for reducing the overall length of high-molecular-weight proteins to low-molecular-weight proteins in the mash. The low-molecular-weight proteins are a necessity for yeast nutrition and the high-molecular-weight-proteins ensure foam stability. Thus it is well-known to the skilled person that protease should be added in a balanced amount which at the same time allows ample free amino acids for the yeast and leaves enough high-molecular-weight-proteins to stabilize the foam. In one aspect, the protease activity is provided by a proteolytic enzymes system having a suitable FAN generation activity including endo-proteases, exopeptidases or any combination hereof, preferably a metallo-protease. Preferably, the protease has at least 50%, more preferably at least 60%, more preferably at least 70%, more preferably at least 80%, more preferably at least 85%, more preferably at least 90%, more preferably at least 91%, more preferably at least 92%, more preferably at least 93%, more preferably at least 94%, more preferably at least 95% more preferably at least 96%, more preferably at least 97% more preferably at least 98%, and most preferably at least 99% or even 100% identity to the amino acid sequence shown in SEQ ID NO:6 described in WO9967370. In another aspect, the protease is Neutrase® available from Novozymes A/S. Proteases may be added in the amounts of, 0.0001-1000 AU/kg DS, preferably 1-100 AU/kg DS and most preferably 5-25 AU/kg dry weight cereal(s). The proteolytic activity may be determined by using denatured hemoglobin as substrate. In the Anson-Hemoglobin method for the determination of proteolytic activity, denatured hemoglobin is digested, and the undigested hemoglobin is precipitated with trichloroacetic acid (TCA). The amount of the TCA soluble product is determined by using phenol reagent, which gives a blue color with tyrosine and tryptophan. One Anson Unit (AU) is defined as the amount of enzyme which under standard conditions (i.e. 25° C., pH 7.5 and 10 min. reaction time) digests hemoglobin at an initial rate such that there is liberated an amount of TCA soluble product per minute which gives the same colour with phenol reagent as one milliequivalent of tyrosine.

Cellulase (E.C. 3.2.1.4)

The cellulase may be of microbial origin, such as derivable from a strain of a filamentous fungus (e.g., *Aspergillus, Trichoderma, Humicola, Fusarium*). Specific examples of cellulases include the endoglucanase (endoglucanase I) obtainable from *H. insolens* and further defined by the amino acid sequence of FIG. 14 in WO 91/17244 and the 43 kD *H. insolens* endoglucanase described in WO 91/17243.

A particular cellulase to be used in the processes of the invention may be an endo-glucanase, such as an endo-1,4-beta-glucanase. Especially contemplated is the beta-glucanase shown in SEQ.ID.NO: 2 in WO 2003/062409 and homologous sequences. Commercially available cellulase preparations which may be used include CELLUCLAST®, CELLUZYME®, CEREFLO® and ULTRAFLO® (available from Novozymes A/S), LAMINEX™ and SPEZYME® CP (available from Genencor Int.) and ROHAMENT® 7069 W (available from Röhm, Germany). Beta-glucanases may be added in the amounts of 1.0-10000 BGXU/kg DS, preferably from 10-5000 BGXU/kg DS, preferably from 50-1000 BGXU/kg DS and most preferably from 100-500 BGXU/kg DS.

One Beta Glucanase Unit (BGXU) corresponds to the quantity of enzyme required to produce 1 micromole of reducing sugars per minute under standard conditions (incubation at 30° C. for 10 minutes at pH 4.40).

Xylanase:

Xylanases are known in the art. In one aspect, xylanase activity is provided by a xylanase from glycosyl hydrolase family 10. In one aspect, the xylanase has at least 50%, more preferably at least 60%, more preferably at least 70%, more preferably at least 80%, more preferably at least 85%, more preferably at least 90%, more preferably at least 91%, more preferably at least 92%, more preferably at least 93%, more preferably at least 94% more preferably at least 95%, more preferably at least 96%, more preferably at least 97% more preferably at least 98%, and most preferably at least 99% or even 100% identity to the xylanase described in WO 94/21785. In another aspect, the xylanase is Shearzyme® from Novozymes A/S. Preferably the xylanase activity in the mash is 0.02-0.1 FXU(S)/g, more preferably 0.04-0.08 FXU(S)/g dry weight cereal(s). The xylanolytic activity can be expressed in FXU(S)-units, determined at pH 6.0 with remazol-xylan (4-O-methyl-D-glucurono-D-xylan dyed with Remazol Brilliant Blue R, Fluke) as substrate. An xylanase sample is incubated with the remazol-xylan substrate. The background of non-degraded dyed substrate is precipitated by ethanol. The remaining blue colour in the supernatant (as determined spectrophotometrically at 585 nm) is proportional to the xylanase activity, and the xylanase units are then determined relatively to an enzyme standard at standard reaction conditions, i.e. Substrate concentration 0.45% w/v, Enzyme concentration 0.04-0.14 FXU(S)/mL at 50.0° C., pH 6.0, and in 30 minutes reaction time. Xylanase activity in FXU(S) is measured relative to a Novozymes FXU(S) enzyme standard (obtainable from Novozymes), comprising the monocomponent xylanase preparation, Shearzyme® from *Aspergillus aculeatus*.

Lipase:

Lipases are known in the art. In one embodiment, the lipase activity is provided by a lipase having activity to triglycerides and/or galactolipids and/or phospholipids. Preferably, the lipase activity is provided by a lipase from *Fusarium* (including *F. oxysporum* and *F. heterosporum*), *Aspergillus* (including *A. tubigensis*), *Rhizopus* (including *R. oryzae*) or *Thermomyces* (including *T. lanuginosus*) or a variant of these. An example is Lipopan X (Lipopan Xtra), a variant of the *Thermomyces lanuginosus* lipase with the substitutions G91A+D96W+E99K+P256V+G263Q+L264A+1265T+G266D+T267A+L269N+270A+271G+272G+273F (+274S), described in WO2004099400A2. In another aspect, the lipase is a lipase/phospholipase from *Fusarium oxysporum*, described in EP 869167, available from Novozymes A/S as Lipopan® F. In a specially preferred embodiment of the invention the lipase is Lipozyme TL® or Lipolase®, this lipase has a significantly good effect on filtration speed and haze reduction and is available from Novozymes A/S, Denmark. The lipase may also be Lipex®, a variant of Lipozyme, available from Novozymes A/S Denmark. The lipases degrade the lipid from barley e.g. the triglycerides into partial glycerides and free fatty acids. This leads to a lower turbidity and much improved mash filtration and lautering properties. Preferably, the lipase activity in the mash is 0-50 LU/g, such as 0-40 LU/g, such as 0-30 LU/g, such as 0-20 LU/g dry weight cereal(s). One Lipase Unit (LU) is the amount of enzyme which liberates 1 micromole of titrable butyric acid per minute at 30.0° C.; pH 7.0; with Gum Arabic as emulsifier and tributyrine as substrate.

The enzymes may be added as enzyme compositions. They may consist of one enzyme or more than one enzyme or more than one enzyme compositions. The enzyme composition, in addition to the enzyme(s), may also contain at least one other substance, for example but not limited to buffer, surfactants etc. The enzyme compositions may be in any art-recognized form, for example, solid, liquid, emulsion, gel, or paste. Such forms are known to the person skilled in the art. In one aspect of the invention more than one enzyme composition, each containing different enzymes may be added. In another aspect of the invention, one enzyme composition containing all the necessary enzymes may be added. In yet another aspect of the invention, one enzyme composition containing a few of the enzymes and at least one another composition containing some or all of the rest of the enzymes may be added. The enzymes may be added at the same time or in sequence one after another or even as a combination of two enzymes and one enzyme separately, one after the other.

The invention is further illustrated in the following example, which is not intended to be in any way limiting to the scope of the invention as claimed.

Materials and Methods:

Glucoamylase Activity:

Glucoamylase activity may be measured in AGU Units.

The Glucoamylase Unit (AGU) is defined as the amount of enzyme, which hydrolyzes 1 micromole maltose per minute under the standard conditions (37° C., pH 4.3, substrate: maltose 100 mM, buffer: acetate 0.1 M, reaction time 6 minutes as set out in the glucoamylase incubation below), thereby generating glucose.

| Glucoamylase incubation: | |
| --- | --- |
| Substrate: | maltose 100 mM |
| Buffer: | acetate 0.1M |
| pH: | 4.30 ± 0.05 |
| Incubation temperature: | 37° C. ± 1 |
| Reaction time: | 6 minutes |
| Enzyme working range: | 0.5-4.0 AGU/mL |

The analysis principle is described by 3 reaction steps:

Step 1 is an enzyme reaction:

Glucoamylase, EC 3.2.1.3 (exo-alpha-1,4-glucan-glucohydrolase), hydrolyzes maltose to form alpha-D-glucose. After incubation, the reaction is stopped with NaOH.

Step 2 and 3 result in an endpoint reaction:

Glucose is phosphorylated by ATP, in a reaction catalyzed by hexokinase. The glucose-6-phosphate formed is oxidized to 6-phosphogluconate by glucose-6-phosphate dehydrogenase. In this same reaction, an equimolar amount of NAD+ is reduced to NADH with a resulting increase in absorbance at 340 nm. An autoanalyzer system such as Konelab 30 Analyzer (Thermo Fisher Scientific) may be used.

| Colour reaction | |
| --- | --- |
| Tris | approx. 35 mM |
| ATP | 0.7 mM |
| NAD$^+$ | 0.7 mM |
| Mg$^{2+}$ | 1.8 mM |
| Hexokinase | >850 U/L |
| Glucose-6-P-DH | >850 U/L |
| pH | approx. 7.8 |
| Temperature | 37.0° C. ± 1.0° C. |
| Reaction time | 420 sec |
| Wavelength | 340 nm |

Chemicals used as buffers and substrates were commercial products of at least reagent grade.

Enzymes:

The glucoamylases of Seq ID No: 1, Seq ID No: 2, Seq ID No: 3 and Seq ID No: 4 were made using standard recombinant techniques, e.g., as found in WO 2011/127802.

EXAMPLES

Example 1: Temperature Optimum of Glucoamylases

The temperature optimum of glucoamylase of various sequences was determined by the enzymes' ability of releasing glucose during incubation at 32 to 85° C. at pH 6.0. 4 different glucoamylases Seq ID No: 1, Seq ID No: 2, Seq ID No: 3, Seq ID No: 4 were used. 10 µL of enzyme solution (0.5 mg glucoamylase/mL in 10 mM NaOAc buffer pH 6.0 with 0.02% Triton X-100) was mixed with 190 µL substrate solution (10.5% maltodextrin DE11 in 50 mM NaOAc). The mixture was incubated at 32, 55, 60, 65, 70, 80 or 85° C. for 1 hour. After incubation 10 µL of this sample was mixed with 190 µL Milli-Q water (×20 dilution) for all samples except the 32° C. incubated sample was only diluted ×5. The glucose concentration (mg/mL) in the sample was determined by the enzymatic muratose-GOD assay (Wako Autokit Glucose, 439-90901).

10 µL of the diluted sample was transferred to a 96 well plate, 200 µL stop reagent was added and absorbance measured at 505 nm. Absorbance was converted to mg/mL glucose applying a glucose standard curve. The results are tabulated in table 1 below:

TABLE 1

Temperature optimum of glucoamylases measured at pH 6.0 by the formation of glucose (mg/mL) using maltodextrin as substrate.

| | Seq ID no 3 | | Seq ID no 1 | | Seq ID no 2 | | Seq ID no 4. | |
| --- | --- | --- | --- | --- | --- | --- | --- | --- |
| ° C. | mg/mL glucose | Residual activity in % (max = 100%) | mg/mL glucose | Residual activity in % (max = 100%) | mg/mL glucose | Residual activity in % (max = 100%) | mg/mL glucose | Residual activity in % (max = 100%) |
| 32 | 3.62 | 17.24 | 3.84 | 15.04 | 3.36 | 26.99 | 3.80 | 20.45 |
| 55 | 15.85 | 75.48 | 15.25 | 59.71 | 10.55 | 84.74 | 14.71 | 79.17 |
| 60 | 20.44 | 97.33 | 19.82 | 77.60 | 12.45 | 100.00 | 18.58 | 100.00 |
| 65 | 21.0 | 100.00 | 22.57 | 88.37 | 10.11 | 81.20 | 16.63 | 89.50 |
| 70 | 14.47 | 68.90 | 25.54 | 100.00 | 2.31 | 18.55 | 5.75 | 30.95 |
| 75 | 3.73 | 17.76 | 23.13 | 90.56 | 0.47 | 3.78 | 1.40 | 7.53 |
| 80 | 1.20 | 5.71 | 8.29 | 32.46 | 0.26 | 2.09 | 0.65 | 3.50 |
| 85 | 0.63 | 3.00 | 1.57 | 6.15 | 0.17 | 1.37 | 0.37 | 1.99 |

From the table, it appears that the glucoamylase of Seq ID No 1 demonstrates a higher temperature optimum (70° C.) than the other glucoamylases measured (60-65° C.).

Example 2: Effect of Various Glucoamylases in Wort Production

The mashing was carried out in duplicate and was downscaled mimicking a typical lab scale mashing set-up. Maize grits and well modified malt were ground with a particle size of 0.2 mm. 0.150 g maize grits and 0.015 g well modified malt was mixed with 660 µL water added 100 ppm $Ca^{2+}$. This fraction was incubated with shaking (1200 rpm) according to the following procedure (cereal cooking): 10 min at 45° C., increase to 80° C. with 5° C. per 5 min, incubation for 5 min at 80° C., increase to 90° C. with for 5° C. per 5 min, incubate at 90° C. for 10 minutes. To this liquefied corn fraction was added 666.7 µL water containing 60 ppm $Ca^{2+}$ and 0.169 g well modified malt. Glucoamylase from various sources described above, was added to the mash with and without simulated lautering according to Table 2 and Table 3.

Saccharification was carried out as follows: 2 hours at 64° C., increase to 75° C. with 5° C. per 5 min, incubation for 15 min at 75° C. The incubation was either terminated by cooling to 20° C. or continued by increasing the temperature to 78° C. incubating for additional 2 hours before cooling to 20° C. (simulated lautering). After termination of incubation, the weight of each sample was adjusted to a total of 2.0 g, the sample was centrifuged for 5 min at 14.000 rpm and the supernatant (wort) was analyzed for extract level and sugar profile by HPLC. The results are tabulated in table 2 below. The terms "DP1" (Degree of polymerization 1) denotes glucose or fructose, "DP2" denotes maltose and DP3 denotes maltotriose. The terms "DP4+" or "DP4/4+" denote dextrin, or maltooligosaccharides of a polymerization degree of 4 or higher.

TABLE 2

Sugar Profile (% of total) of wort obtained at end of mashing under simulated lautering

| Enzyme | Dosage (mg EP/g total grist) | % DP4+ (non-fermentable fraction) | % DP3 | % DP2 | % DP1[a] (glucose) |
|---|---|---|---|---|---|
| Control | 0 | 18.71 | 14.35 | 55.34 | 11.61 |
| Seq ID No 2 | 0.025 | 17.53 | 4.00 | 50.25 | 28.22 |
| Seq ID No 2 | 0.1 | 14.59 | 1.96 | 22.41 | 61.04 |
| Seq ID No 2 | 0.2 | 9.89 | 1.68 | 5.95 | 82.47 |
| Seq ID No 2 | 0.3 | 6.57 | 1.23 | 2.05 | 90.14 |
| Seq ID No 2 | 0.5 | 4.29 | 0.49 | 1.47 | 92.75 |
| Seq ID No 1 | 0.05 | 13.17 | 2.15 | 36.87 | 47.82 |
| Seq ID No 1 | 0.1 | 9.16 | 1.99 | 16.45 | 72.39 |
| Seq ID No 1 | 0.2 | 4.88 | 1.68 | 3.69 | 89.75 |
| Seq ID No 1 | 0.3 | 3.27 | 1.41 | 2.27 | 93.05 |
| Seq ID No 1 | 0.5 | 2.10 | 1.20 | 1.34 | 95.37 |
| Seq ID No 1 | 1.0 | 1.91 | 1.05 | 3.32 | 93.72 |
| Seq ID No 3 | 0.25 | 16.12 | 2.57 | 41.76 | 39.55 |
| Seq ID No 3 | 2.0 | 0.54 | 1.40 | 2.43 | 95.63 |
| Seq ID No 4 | 0.1 | 16.41 | 2.72 | 44.46 | 36.41 |
| Seq ID No 4 | 0.75 | 4.05 | 1.38 | 2.48 | 92.1 |

[a]includes small amounts of fructose.

Form table 2, it can be see that glucoamylase of Seq ID No 1 performs superior to the other glucoamylases in mashing followed by simulated lautering. In order to reach the same level of DP4+ half the amount of glucoamylase of Seq ID No 1 is required in comparison to glucoamylase of Seq ID No 2.

TABLE 3

Sugar Profile (% of total) of wort at end of mashing without simulated lautering.

| Enzyme | Dosage (mg EP/g total grist) | % DP4+ (non-fermentable fraction) | % DP3 | % DP2 | % DP1[a] (glucose) |
|---|---|---|---|---|---|
| Control | 0 | 18.56 | 14.03 | 55.71 | 11.69 |
| Seq ID No 2 | 0.025 | 17.19 | 4.05 | 50.89 | 27.87 |
| Seq ID No 2 | 0.25 | 7.30 | 1.50 | 2.20 | 88.9 |
| Seq ID No 2 | 0.5 | 3.59 | 0.76 | 1.75 | 93.9 |
| Seq ID No 1 | 0.1 | 12.85 | 2.19 | 34.66 | 50.3 |
| Seq ID No 1 | 0.16 | 11.50 | 2.20 | 25.30 | 61.0 |
| Seq ID No 1 | 0.32 | 5.80 | 1.90 | 3.30 | 89.0 |
| Seq ID No 1 | 0.5 | 2.62 | 1.30 | 1.80 | 94.28 |
| Seq ID No 1 | 1.0 | 1.87 | 1.04 | 2.70 | 94.4 |
| Seq ID No 3 | 0.25 | 16.35 | 2.50 | 42.09 | 39.06 |
| Seq ID No 3 | 2.0 | 4.08 | 1.24 | 2.16 | 92.52 |
| Seq ID No 4 | 0.1 | 16.46 | 2.70 | 44.82 | 36.02 |
| Seq ID No 4 | 0.75 | 4.28 | 1.36 | 2.37 | 91.97 |

[a]includes small amounts of fructose.

From table 3 above, it appears that glucoamylase of Seq ID No 1 does not perform better than glucoamylase of Seq ID No 2, in the absence of simulated lautering.

Example 3: Effect of Lautering Temperature and pH on Concentration of DP1 Fraction The experiment was performed with 55% malt/45% corn and using a saccharification time of 4 hours. The glucoamylase of Seq ID No 1 was dosed at 0.3 mg EP/total grist (1.44 AGU/total grist). The effect of varying lautering temperatures and pH on the DP1 fraction was studied. The results are given in table 4 below:

TABLE 4

Effect of varying the lautering temperature and pH on the concentration of DP1 fractions

| pH | Lautering Temperature (° C.) | DP1 fraction (as a % of total sugar) | |
|---|---|---|---|
| | | Trial 1 | Trial 2 |
| 5.0 | 80 | 91.8 | 91.8 |
| 5.3 | 80 | 92.3 | 92.2 |
| 6.0 | 80 | 89.2 | 89.9 |
| 5.0 | 78 | 93.7 | 92.8 |
| 5.3 | 78 | 92.8 | 92.7 |
| 6.0 | 78 | 92.2 | 92.3 |

Example 4: Effect of Glucoamylase in Combination with Pullulanase

The mashing experiment carried out in duplicate was downscaled mimicking a typical lab scale mashing set-up. Maize grits and well modified malt was grinded with a particle size of 0.2 mm. 0.150 g maize grits and 0.015 g well modified malt was mixed with 660 µL water added 100 ppm $Ca^{2+}$. This fraction was incubated with shaking (1200 rpm) according to the following procedure (cereal cooking): 10 min at 45° C., increase to 80° C. with 5° C. per 5 min, incubation for 5 min at 80° C., increase to 90° C. with for 5° C. per 5 min, incubate at 90° C. for 10 minutes. This liquefied corn fraction was added 666.7 µL water containing 60 ppm $Ca^{2+}$ and 0.169 g well modified malt.

Exogenously supplied enzymes were added at this point and according to Table 5.

The pullulanase used was of Sequence ID No 3 disclosed in WO2009075682.

Saccharification was carried out as follows: 2 hours at 64° C., increase to 75° C. with 5° C. per 5 min, incubation for 15 min at 75° C. The incubation was either terminated by cooling to 20° C. or continued by increasing the temperature to 78° C. incubating for additional 2 hours before cooling to 20° C. (simulated lautering). After termination of incubation, the weight of each sample was adjusted to a total of 2.0 g, the sample was centrifuged for 5 min at 14.000 rpm and the supernatant (wort) was analyzed for extract level and sugar profile by HPLC.

TABLE 5

Wort sugar profile of mash treated with glucoamylase with and without pullulanase.

| Conditions | Glucoamylase of Seq ID no 1 | Pullulanase | DP1 (glu) | DP1 (fru) | DP2 | DP3 | DP4+ |
|---|---|---|---|---|---|---|---|
| Mashing with no simulated lautering | 0.85 AGU/g total grist | — | 77.0 | 1.0 | 11.5 | 1.9 | 8.6 |
| Mashing with no simulated lautering | 0.85 AGU/g total grist | 0.57 PUN-G/g total grist | 77.6 | 1.4 | 14.9 | 3.0 | 3.1 |
| Mashing with simulated lautering | 0.85 AGU/g total grist | — | 89.6 | 1.1 | 3.2 | 1.6 | 4.5 |
| Mashing with simulated lautering | 0.85 AGU/g total grist | 0.57 PUN-G/g total grist | 87.7 | 1.5 | 5.8 | 2.4 | 2.6 |

The results clearly demonstrate a benefit of adding pullulanase on top of glucoamylase in mashing.

The invention claimed is:

1. A method of producing a brewer's wort comprising adding to a mash, a glucoamylase that is at least 90% identical to the sequence shown in SEQ ID NO: 1, wherein the mash comprises malted and unmalted grain, wherein the glucoamylase is added in an amount of less than 0.4 mg enzyme protein per gram of the total grist and wherein a pullulanase is not added to the mash.

2. The method according to claim 1, wherein mashing comprises an incubation step of at least 65° C. for at least 20 minutes.

3. The method according to claim 1, wherein the pH of the mash is about 4.6 to about 6.4.

4. The method according to claim 1, wherein the glucoamylase has a temperature optimum of above 65° C.

5. The method according to claim 1, further comprising adding a protease.

6. The method according to claim 1, further comprising adding a xylanase.

7. The method according to claim 1, further comprising adding a lipase.

8. The method according to claim 1, further comprising adding a cellulase.

9. The method according to claim 1, further comprising adding an amylase.

10. The method according to claim 1, further comprising adding a beta glucanase.

11. The method according to claim 1, wherein the wort has more than 80% glucose, compared to the total carbohydrate content of the wort.

12. The method according to claim 1, wherein the glucoamylase is obtainable from *Penicillium*.

13. The method according to claim 1, wherein the glucoamylase is at least 95% identical to the amino acid sequence shown in SEQ ID NO: 1.

14. The method according to claim 1, wherein the glucoamylase is added in an amount of less than 0.3 mg enzyme protein per gram of the total grist.

15. The method according to claim 1, wherein the glucoamylase is added in an amount of less than 0.2 mg enzyme protein per gram of the total grist.

16. The method according to claim 1, wherein the glucoamylase is added in an amount of less than 0.15 mg enzyme protein per gram of the total grist.

17. A method of producing a brewer's wort comprising adding to a mash, a glucoamylase that is at least 90% identical to the sequence shown in SEQ ID NO: 1, wherein the mash comprises malted and unmalted grain, wherein the glucoamylase is added in an amount of less than 0.4 mg enzyme protein per gram of the total grist and wherein a pullulanase is not added in the production method.

* * * * *